(12) United States Patent
Stauffer

(10) Patent No.: US 8,581,010 B2
(45) Date of Patent: *Nov. 12, 2013

(54) FORMATION OF ETHANOL FROM METHANOL

(76) Inventor: John E. Stauffer, Greenwich, CT (US)

( * ) Notice: Subject to any disclaimer, the term of this patent is extended or adjusted under 35 U.S.C. 154(b) by 301 days.

This patent is subject to a terminal disclaimer.

(21) Appl. No.: 13/100,345

(22) Filed: May 4, 2011

(65) Prior Publication Data

US 2012/0283488 A1    Nov. 8, 2012

(51) Int. Cl.
*C07C 29/32* (2006.01)

(52) U.S. Cl.
USPC .............................. 568/902; 568/909; 568/914

(58) Field of Classification Search
USPC .......................................... 568/902, 909, 914
See application file for complete search history.

(56) References Cited

U.S. PATENT DOCUMENTS

| 4,562,174 | A | * | 12/1985 | Stiles | 502/174 |
| 4,825,004 | A | * | 4/1989 | Rutzen et al. | 568/864 |
| 4,913,842 | A | * | 4/1990 | Yoneoka et al. | 252/373 |
| 5,395,991 | A | * | 3/1995 | Scarlett et al. | 568/864 |
| 5,449,696 | A | * | 9/1995 | Dandekar et al. | 518/706 |
| 5,453,412 | A | * | 9/1995 | Deckers et al. | 502/342 |
| 5,663,429 | A | * | 9/1997 | Yamaseki et al. | 562/519 |
| 6,114,279 | A | * | 9/2000 | Fukui et al. | 502/342 |
| 6,140,545 | A | * | 10/2000 | Merger et al. | 568/799 |
| 6,632,330 | B1 | * | 10/2003 | Colley et al. | 203/29 |
| 7,977,272 | B2 | * | 7/2011 | Miller et al. | 502/213 |
| 2008/0269519 | A1 | * | 10/2008 | Miller et al. | 562/519 |

* cited by examiner

*Primary Examiner* — Sudhakar Katakam
*Assistant Examiner* — Pancham Bakshi
(74) *Attorney, Agent, or Firm* — Young Basile Hanton & MacFarlane PC

(57) ABSTRACT

A process is disclosed for the production of ethanol from methanol whereby methanol is condensed in the gas phase over a heterogeneous catalyst to produce ethanol and water.

1 Claim, 2 Drawing Sheets

FORMATION OF ETHANOL FROM METHANOL

FIELD OF THE INVENTION

The invention relates to a process for the manufacture of ethanol from methanol. In the process, methanol vapor is passed over a heterogeneous catalyst at an elevated temperature to produce ethanol and water.

BACKGROUND OF THE INVENTION

There are two principal routes for the commercial production of ethanol. One procedure is based on petrochemical technology. Starting with Ethylene, ethanol is produced by means of the catalytic hydration of this olefin. While this process is efficient, it has the disadvantage of depending on a supply of ethylene, which historically has experienced price volatility.

The second method relies on the fermentation of sugar, either derived from corn or sugar cane. A major drawback to fermentation processes is the fluctuation in the prices of the commodities, corn and sugar. To a large extent, the fermentation industry has depended on government subsidies to remain competitive.

SUMMARY OF THE INVENTION

A process is provided for the production of ethanol from methanol. In the process. Methanol is vaporized and passed over a compound catalyst at an elevated temperature to produce ethanol and water. After the product gases are condensed, the ethanol and water are separated by distillation.

The catalyst comprises an intimate mixture of three separate catalysts: copper oxide and zinc oxide on an alumina support; rhodium promoted with iodide; and copper chromite. The intermingled catalysts are placed in a shell and tube reactor or other type of reactor of suitable design. In this manner, the heat of reaction can effectively be removed.

The reaction temperature is generally in the range of 250° C. to 350° C. but may extend either below or above this range for given reasons. The process is operated at a moderate pressure with a nominal pressure in the range of 1 to 60 atmospheres. This range is subject to modification depending on reaction kinetics.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying photographs, the latter being briefly described hereinafter.

BRIEF SUMMARY OF THE DRAWINGS

The description herein makes reference to the accompanying drawings wherein like reference numerals refer to like parts throughout the several views and wherein.

DETAILED DESCRIPTION OF THE ILLUSTRATIVE EMBODIMENT

Figure 1:
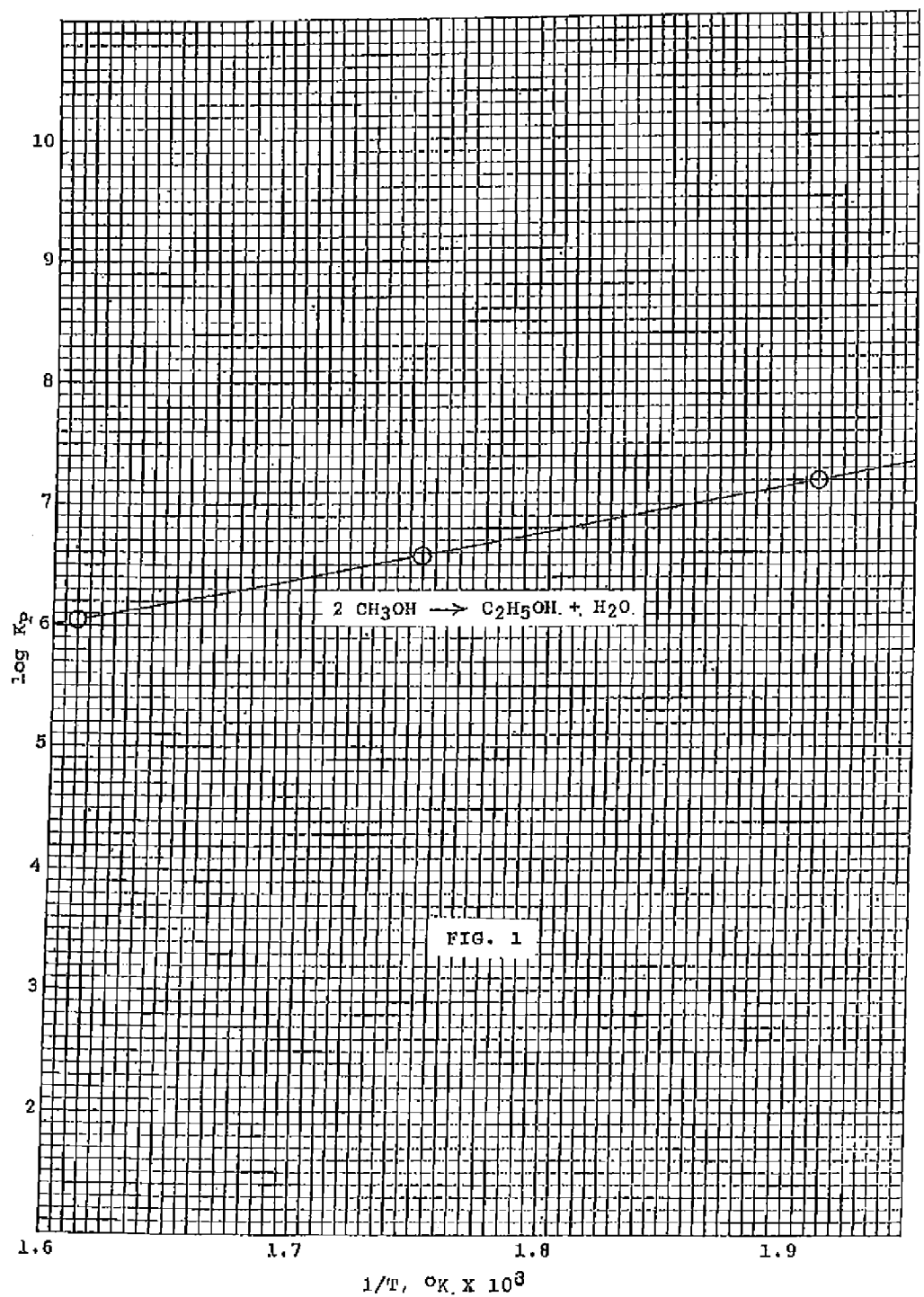
FIG. 1 is a graph showing the equilibrium conversions for the overall reaction at given temperatures.

The process of the present invention comprises three distinct chemical reactions that occur simultaneously and in intimate contact with each other. Thus, the products of one reaction are the reactants in another reaction until the final products are obtained. These three reactions can be expressed by the following equations:

$$CH_3OH \rightarrow CO + 2H_2 \qquad \qquad 1.$$

$$2CH_3OH + CO \rightarrow CH_3COOCH_3 + H_2O \qquad \qquad 2.$$

$$CH_3COOCH_3 + 2H_2 \rightarrow C_2H_5OH + CH_3OH \qquad \qquad 3.$$

In the above equations, $CH_3OH$ is methanol, CO carbon monoxide, $H_2$ hydrogen, $CH_3COOCH_3$ methyl acetate, $H_2O$ water, and $C_2H_5OH$ ethanol.

When the above equations are combined, the following expression is obtained.

$$2CH_3OH \rightarrow C_2H_5OH + H_2O \qquad \qquad 4.$$

The latter equation represents the overall reaction of the process. It shows that two moles of methanol are condensed to provide one mole of ethanol and one mole of water.

The reaction shown by equation 1 is the reverse of the well known synthesis of methanol. This reaction is promoted by a catalyst comprising copper oxide and zinc oxide deposited on a substrate of alumina. The reaction temperature is in the range of 250° C. to 350° C. Unlike the production of methanol from synthesis gas, which requires high pressures, the decomposition of methanol in the present invention occurs at essentially atmospheric pressure.

The standard preparation of acetic acid from methanol and carbon monoxide by carbonylation is shown at equation 2, only in this case the product is methyl acetate instead of acetic acid. Over the years many catalysts have been reported for this reaction, all of which required relatively high temperatures and pressures. A breakthrough occurred when a low pressure methanol carbonylation process was developed based on a catalyst of rhodium promoted with iodide. With this improvement, reaction temperatures as low as 150° C. to 200° C. and pressures in the range of 33 to 65 atmospheres were possible.

Although the direct reduction of organic acids is not practical, their esters react readily with hydrogen to form the corresponding alcohols. This reaction is given in equation 3. Thereby methyl acetate is converted to ethanol and methanol. The catalyst for this reaction is copper chromite and the reaction temperature is in the neighborhood of 250° C. Because this chemistry is normally practiced in the liquid phase, high pressures of hydrogen are employed. However, with the present invention, which takes place in the gas phase, excessive pressures are not anticipated.

The conditions necessary for the overall reaction given by equation 4 are a composite of the conditions specified for the individual reactions. Fortunately, these conditions nicely coincide with one another. Therefore, the recommended temperature for the process is in the range of 250° C. to 350° C. and the pressure is in the range of 1 to 60 atmospheres. The catalyst is a composite of the catalysts of the individual reactions. Thus, the catalyst bed is comprised of an intimate mixture of pellets or granules of the separate catalysts.

Equilibrium conditions for the overall reaction are highly favorable. FIG. 1 presents data for equilibrium constants for the recommended temperature range. As seen from the graph, log Kp is 7.20 at 250° C. and 6.03 at 350° C. These data indicate that process of the present invention will provide high conversions and yields of product, thus maximizing the efficiency of the operation.

Figure 2:
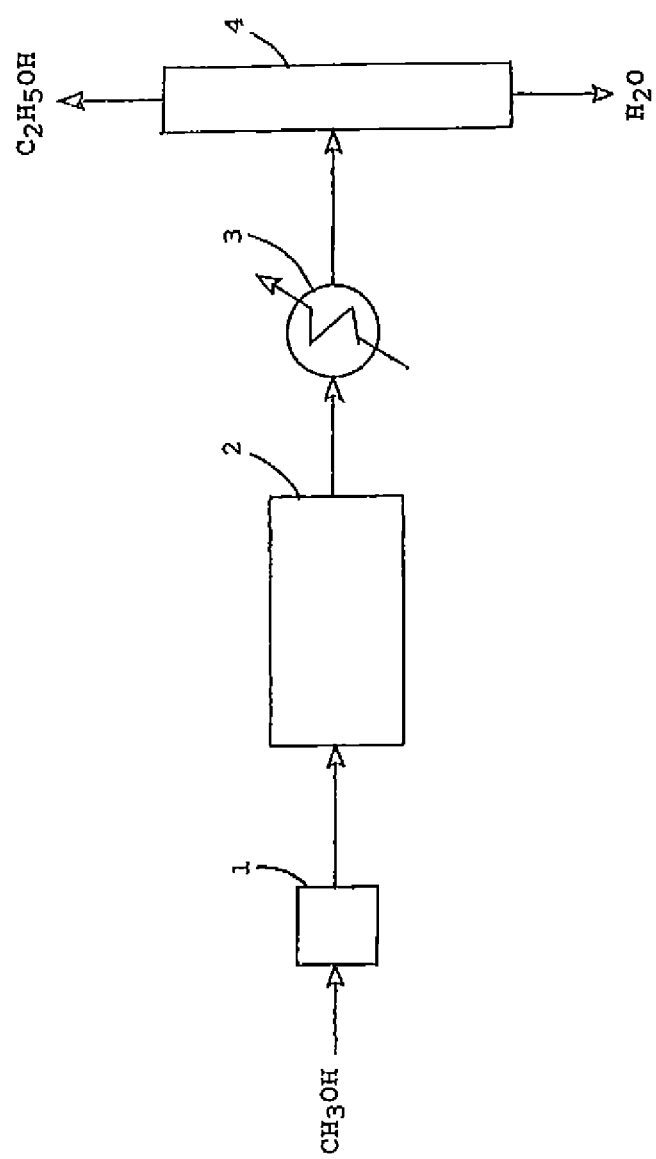
FIG. 2 provides a flow sheet of the process, identifying the principal steps of the operation.

A practical system for calving out the process is shown in FIG. 2. Incoming methanol feed is vaporized in preheater 1 before entering reactor 2. The effluent gases from the reactor are cooled in heat exchanger 3 to condense ethanol and water, which are fractionated in distillation column 5. The product ethanol may be further processed in equipment (not shown) to produce absolute alcohol.

The advantages of the present invention include its relative simplicity. The projected low capital investment and reduced operating costs are definite plusses. The wide availability of the raw material methanol is an important factor. With these advantages, the process has the capability to compete with current technology.

What is claimed is:

1. A process for the manufacture of ethanol from methanol in a single step consisting of the gas phase reaction of methanol over a heterogeneous catalyst comprising a mixture of copper zinc aluminum oxides, iodine promoted rhodium, and copper chromite, at a temperature in the range of 250° C. to 350° C. and a pressure of 1 to 60 atmospheres.

* * * * *